United States Patent [19]

Yuen et al.

[11] Patent Number: 4,579,960

[45] Date of Patent: Apr. 1, 1986

[54] STABLE SOLUTIONS CONTAINING THIMEROSAL

[75] Inventors: Pui-Ho Yuen, Edison; Shreeram Agharkar, Montville, both of N.J.

[73] Assignee: Schering Corporation, Kenilworth, N.J.

[21] Appl. No.: 607,845

[22] Filed: May 7, 1984

[51] Int. Cl.[4] .............................................. C07F 3/12
[52] U.S. Cl. ....................................... 556/2; 514/496
[58] Field of Search ........................... 260/434; 556/2; 514/496

[56] References Cited

U.S. PATENT DOCUMENTS

| | | | |
|---|---|---|---|
| 1,672,615 | 6/1928 | Kharasch | 260/434 |
| 2,012,820 | 8/1935 | Kharasch | 260/434 X |
| 2,411,815 | 11/1946 | Sowa | 260/434 X |
| 2,618,645 | 11/1952 | Bowles | 260/434 |

OTHER PUBLICATIONS

The Merck Index, Merck & Co., Inc., Rahway, N.J., 10th Edition, pp. 330, 331, 144, 1070, 1110 and 1334 (1983).

*Primary Examiner*—Helen M. S. Sneed
*Attorney, Agent, or Firm*—Warrick E. Lee, Jr.

[57] ABSTRACT

Buffered aqueous solution of thimerosal wherein the buffer is citric acid and sodium citrate having a pH between 3.5 and 7.

3 Claims, No Drawings

STABLE SOLUTIONS CONTAINING THIMEROSAL

The present invention relates to solutions containing thimerosal having greater stability than those of the prior art. Thimerosal, also called merthiolate, is a very effective antimicrobial. It may be used as a perservative for solutions intended for use in the eye or nose. However, when formulated with certain common buffers, such as phosphates and acetates, thimerosal degrades too quickly.

The present invention is based on the finding that thimerosal solutions containing specific buffer ingredients and having a pH in a specific range have much greater stability.

SUMMARY OF THE INVENTION

The present invention comprises a stable solution comprising:
(a) thimerosal,
(b) a compound selected from the group consisting of citric acid monohydrate, anhydrous citric acid, and combinations thereof,
(c) a compound selected from the group consisting of sodium citrate dihydrate, anhydrous sodium citrate and combinations thereof and
(d) water,
said solution having a pH between 3.5 and 7.

DETAILED DESCRIPTION OF THE INVENTION

The inventive solutions are preferably prepared by mixing two solutions. The first solution contains either citric acid monohydrate or anhydrous citric acid at a concentration of 0.002M. The second solution contains either sodium citrate dihydrate or anhydrous sodium citrate at a concentration of 0.002M. The two solutions are mixed together in selected volume ratios to yield a buffered solution having the desired pH as illustrated in the following table.

| Parts by Volume of 0.002 M citric acid Solution | Parts by Volume of 0.002 M sodium citrate Solution | Resulting pH |
| --- | --- | --- |
| 1 | 0.21 | 3.5 |
| 1 | 0.88 | 4.5 |
| 1 | 2.23 | 5.5 |
| 1 | 9.26 | 6.5 |

Next, antimicrobial effective amounts of thimerosal and any active ingredients are added to the resulting mixture.

The resulting solution should have a pH in the range of 3.5 to 7, more preferably 3.5 to 5 and most preferably 4.5 to 5.

EXAMPLES

| Ingredient | Example 1 mg/ml | Example 2 mg/ml |
| --- | --- | --- |
| Thimerosal | 0.02 | 0.02 |
| Citric acid monohydrate | 0.22 | 0.23 |
| Sodium citrate dihydrate | 0.28 | 0.27 |
| Purified Distilled water q.s. ad: | 1 ml | 1 ml |
| pH | 4 | 4.5 |

Any active ingredient compatible with thimerosal and the citrate buffer system may be used. Examples of active ingredients are pilocarpine (present in a concentration of about 0.25 to 10 weight percent), beclomethasone dipropionate (present in a concentration of, for example, 0.044 weight precent) and prednisolone sodium phosphate (present in a concentration of, for example, 0.5 weight percent).

The solutions of Examples 1 and 2 with no additional ingredients are believed useful for disinfecting soft contact lenses.

The contact lenses are disinfected by immersing the contact lenses in the solution of Examples 1 and 2.

What is claimed is:
1. A stable solution comprising
   (a) thimerosal,
   (b) a compound selected from the group consisting of citric acid mononhydrate, anhydrous citric acid, and combinations thereof,
   (c) a compound selected from the group consisting of sodium citrate dihydrate, anhydrous sodium citrate and combinations thereof and
   (d) water,
   said solution having a pH between 3.5 and 7.
2. The solution of claim 1 further comprising an active ingredient.
3. The solution of claim 2 wherein the active ingredient is selected from the group consisting of pilocarpine, beclomethasone dipropionate, and prednisolone sodium phosphate.

* * * * *